United States Patent [19]

Dowd

[11] Patent Number: 4,956,353

[45] Date of Patent: Sep. 11, 1990

[54] KOJIC ACID AND ESTERS AS INSECTICIDE SYNERGISTS

[75] Inventor: Patrick F. Dowd, Peoria, Ill.

[73] Assignee: The United States of America as represented by the Secretary of Agriculture, Washington, D.C.

[21] Appl. No.: 207,589

[22] Filed: Jun. 16, 1988

[51] Int. Cl.$^5$ .................... A01N 35/06; A01N 37/18; A01N 43/08; A01N 43/16

[52] U.S. Cl. ........................................ 514/65; 514/66; 514/460; 514/469; 514/479; 514/481; 514/531

[58] Field of Search .................... 514/65, 66, 531, 481, 514/479, 469, 460

[56] References Cited

PUBLICATIONS

E. L. Mayer et al., "Nicotine Insecticides, Part II—Search for Activators," USDA-ARS-Bur. Entomol. Plant Quar. Bull. E-709, pp. 1-16 (Dec. 1946).

Raimon L. Beard et al., "Kojic Acid as an Insecticidal Mycotoxin," J. Invert. Pathol. 14: 53-59 (1969).

"Miscellaneous Aspergillus Toxins," in Microbial Toxins, vol. VI, Alex Ciegler, Solomon Kadis, and Samuel J. Ajl (eds.), Chapter 3, pp. cover, 207, 234-251, 294-295, Academic Press, New York (1971).

V. F. Wright et al., "Mycotoxins and Other Fungal Metabolites as Insecticides," in Microbial and Viral Pesticides, Edouard Kurstak (ed.), Chapter 17, pp. cover, 559-583, Marcel Dekker, Inc., New York (1982).

Amira T. Eldefrawi et al., "Receptors for γ-Aminobutyric Acid and Voltage-Dependent Chloride Channels as Targets for Drugs and Toxicants," Faseb J., 1: 262-271 (1987).

R. D. O'Brien, "Carbamates," in Insecticides: Action and Metabolism, Chapter 5, pp. cover, 86-88, 97-98, 152-153, 156-157, 169-171, Academic Press, New York (1967).

D. M. Soderlund et al., "Metabolism of Pyrethrins and Pyrethroids in Insects," in Progress in Pesticide Biochemistry and Toxicology, vol. 3, D. H. Hutson and T. R. Roberts (eds.), Chapter 8, pp. 401-435, John Wiley & Sons, Ltd. (1983).

Ronald J. Kuhr et al., "Metabolism," in Carbamate Insecticides: Chemistry, Biochemistry, and Toxicology, Chapter 7, pp. cover, 143, 155-156, 178-182, 200, CRC Press, Inc., Cleveland, Ohio (1976).

Elzie McCord, Jr. et al. "The Mechanisms of Carbaryl Resistance in the Fall Armyworm, *Spodoptera frugiperda* (J. E. Smith)," Pestic. Biochem. Physiol., 27: 114 ∝ 122 (1987).

*Primary Examiner*—John W. Rollins
*Assistant Examiner*—W. Catchpole
*Attorney, Agent, or Firm*—M. Howard Silverstein; John D. Fado; Curtis P. Ribando

[57] ABSTRACT

Kojic acid and its esters have been found to be more effective synergists for pyrethroid and carbamate insecticides on *H. zea* and *S. frugiperda*. Thus they may serve as replacements for the widely used methylene dioxyphenyl compounds such as piperonyl butoxide.

15 Claims, No Drawings

KOJIC ACID AND ESTERS AS INSECTICIDE SYNERGISTS

BACKGROUND OF THE INVENTION

1. Field of the Invention

This invention relates to the use of kojic acid and esters as insecticide synergists.

DESCRIPTION OF THE PRIOR ART

Kojic acid, 5-hydroxy-2-(hydroxymethyl)-4H-pyran-4-one, is produced by a number of fungi. Although potential uses have been extensively investigated, the only sustained interest in kojic acid lies in its importance as an indicator of the potential presence of aflatoxin in grains [Edouard Kurstak, Microbial and Viral Pesticides, Marcel Dekker, Inc., New York, p. 573 (1982)].

Kojic acid has been reported to be a plant growth inhibitor [Nickel et al., Agric. Biol. Chem. 27: 65–68 (1962)] and a weak insecticide and growth inhibitor for the milkweed bug, housefly, and mosquito [Beard et al., J. Invest. Pathol. 14: 53 (1969)]. Mayer et al. [U.S. Dept. Agric. Bur. Entomol. Plant Quarantine #E-709, 16 pp. (1946)] observed that kojic acid was effective as a synergist for certain formulations of nicotine insecticides. Beard et al. [supra] concluded that kojic acid was unlikely to have commercial use as an insecticide because of its low activity; but they suggested that the synergistic activity observed with nicotine might be useful and expanded to other insecticides. Nicotine exerts its action in insects by mimicking acetylcholine, a neural transmitter [R. D. O'Brien, Insecticides Action and Metabolism, Academic Press, pp. 152–153 (1967)]. On the other hand, the mode of action of pyrethroid insecticides is inhibition of the γ-amino-butyric acid receptor and the chloride channel; carbamate insecticides act by inhibition of acetylcholinesterase [Eldefrawi, FASEB J. 1: 262–271 (1987); O'Brien, supra].

Nicotine is detoxified in insects by excretion or oxidation to cotinine [O'Brien, supra, pp. 156–157]. Pyrethroids appear to be metabolized in insects by oxidation of the ester portion of the molecule as well as by hydrolysis of the ester bond [O'Brien, supra, pp. 169–171]. In carbamate insecticides the primary route of detoxification is by hydrolysis, although some hydroxylation has been found [O'Brien, supra, pp. 97–98]. Hydrolysis has been shown to be the major route of detoxification of carbaryl in both susceptible and resistant strains of fall armyworm larvae [Elvie McCord, Jr. and S. J. Yu, Pesticide Biochem. Physiol. 27: 114–122, see Table 4, p. 119 (1987)].

There is no indication in the literature that kojic acid or its esters would be effective in enhancing or synergizing the activity of pyrethrin or carbamate insecticides which affect the insect by different biochemical mechanisms than nicotine and are detoxified by different means.

SUMMARY OF THE INVENTION

I have now discovered that kojic acid and dibenzoyl kojic acid are effective synergists for pyrethrin, allethrin, and carbamate insecticides applied to *Heliothis zea* and *Spodoptera frugiperda*.

In accordance with this discovery, it is an object of the invention to provide new compositions for controlling insects.

A further object of the invention is to provide a new method to synergize the activity of insecticidal agents.

Other objects and advantages of this invention will become obvious from the ensuing description.

DETAILED DESCRIPTION OF THE INVENTION

Kojic acid and kojic acid esters are contemplated in this invention as components of insecticidal compositions wherein they are effective synergists for the insecticidal components of the compositions. Kojic acid is produced in nature by Aspergillus and Penicillum spp. and is also available from synthetic sources. Kojic acid may be purchased from Sigma Chemical Company. Dibenzoyl kojic acid was prepared by the method of Beelik and Purves [Can. J. Chem. 33: 1361–1374 (1956)].

A synergist is herein defined as a material which enhances the activity of other materials such as insecticides so that the overall activity of the mixture is greater than the sum of the individual components.

The potency of these synergized insecticide compositions dictates that they be applied in conjunction with a suitable inert carrier or vehicle as known in the art. Of particular interest are those which are agronomically or pharmaceutically acceptable. Alcohols, ketones, esters, and aqueous surfactant mixtures are illustrative of suitable carriers. Depending on the substrate, target species, mode of application, and type of responsive desired, the concentration of active insecticidal ingredients in the final composition may vary considerably, but typically should be at least about 0.00001% (0.1 ppm); the kojic acid or kojic acid ester synergist should typically be 100 to 1000 times the concentration of insecticide. Factors such as phytotoxicity toward the treated plant and tolerance of nontarget species can be used by the skilled artisan in determining the optimum levels of the ingredients.

Depending on the pest species, concentration of agents, and method of application, the subject synergized insecticide composition acts to control pests by one or more mechanisms, including, for instance, death inducement, growth regulation, sterilization, as well as interference with metamorphosis and other morphogenic functions. Accordingly, the level of active composition is administered in an amount effective to induce one or more of these responses as predetermined by routine testing. When the ultimate response is pest mortality, an "effective amount" or "pesticidally effective amount" is defined to mean those quantities of composition which will result in a significant mortality rate of a test group as compared to an untreated group. The actual effective amount may vary with the species of pest, stage of larval development, the nature of the substrate, the particular insecticidal agent, the amount of kojic acid synergist, the type of vehicle or carrier, the period of treatment, and other related factors.

To be effective, the synergized insecticide composition must be applied to the locus of, or the vicinity of, the pest to be controlled. When the composition is intended as a stomach poison, it is applied in conjunction with its carrier to the pest diet. In the case of plants, the composition will typically be applied to the leaf surfaces or else systemically incorporated. Alternatively, when the composition is to be used as a contact poison, any method of topical application, such as direct spraying on the pest or on a substrate which is likely to be contacted by the pest, would be appropriate. For purposes of treating internal animal parasites, the composition would be internally administered to the host.

The synergized insecticidal composition encompassed herein are effective in controlling a variety of multicellular organisms. Without desiring to be limited thereto, pests of particular interest known to be vulnerable to treatment are agronomically important insects, especially those of the order Lepidoptera.

A typical synergized insecticidal composition contemplated by this invention comprises kojic acid, 25 ppm to 250 ppm, preferably 250 ppm; pyrethroids, 0.1 ppm to 1.0 ppm, preferably 0.25 ppm; and inert ingredients such as solvents and surfactants and inert carriers.

Another synergized insecticidal composition contemplated by this invention comprises kojic acid, 25 ppm to 250 ppm, preferably 250 ppm; allethrin, 0.1 ppm to 1.0 ppm, preferably 0.25 ppm; and inert ingredients such as solvents, surfactants, and inert carriers.

Without desiring to be bound to any particular theory of operation, it is believed that kojic acid and esters act as synergists by inhibiting insect-detoxifying enzymes which are metallo-oxygenases.

The following examples are intended only to further illustrate the invention and are not intended to limit the scope of the invention which is defined by the claims.

EXAMPLE 1

Insects and Diet Preparation

Neonate larvae of *H. zea* and *S. frugiperda* were used for all assays. They were obtained from laboratory colonies reared on pinto bean-based die at 27°±1° C., 40°±10% relative humidity, and a 14:10 light:dark photoperiod.

The diet used to rear the insects was based on a standard pinto bean diet for many species of Lepidoptera; it is composed of the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto bean) were purchased from U.S. Biochemicals Corp. Before use, the beans were soaked in water until saturated. The agar was added to 250 ml of water and brought to a boil. The other ingredients were blended in a Waring blender until uniformly mixed. The hot agar was added, and blending continued until all ingredients were uniformly mixed.

EXAMPLE 2

Synthesis of Dibenzoyl Kojic Acid

Synthesis was based on the "Benzoylation in Pyridine" methods of Beelik and Purves (supra). Kojic acid, benzoyl chloride, and anhydrous pyridine were from Aldrich. To 50 ml of pyridine under nitrogen were added 0.5 g of kojic acid and 1.25 g of benzoyl chloride. After 3 hours, the nitrogen was cut off and the flask was sealed. The entire reaction was allowed to go at room temperature overnight (total of 16 hrs). The solution was added to an equal volume of 5% sulfuric acid in deionized water on ice. Since little precipitate was formed, the solution was partitioned against an equal volume of hexane. The hexane portion was conserved, and the hexane was removed under a stream of nitrogen (eventually into 20-ml vials). The residue was washed 3× with 10 ml of deionized water. The water was evaporated under nitrogen; the residue was redissolved in acetone and transferred to a preweighed vial for recovery [vial 1 yield 1.28 mg, vial 2 yield 1.50 mg, vial 3 yield 0.28 mg (trial sample)]. Melting point was determined to be 115° C. This is similar to the value reported by Beelik and Purves [suPra] when a multiply recrystalized sample was contaminated with benzoic acid (120°-121° C.). Thin layer chromatographic separation on Whatman LK5DF plates in benzene:acetone (80:20) for 15 cm yielded a major spot of rf 0.87 and a faint spot of rf 0.32 (UV 257.3). The minor spot co-chromatographed with benzoic acid. Separating the sample by the HPLC gradient method of Frisvad [J. Chromatogr. 392: 333-347 (1987)] indicated a major peak at 31.9 min (area 45259) and minor peaks at 9.73 (area 3866), 11.68 (area 3108), and 30.4 (area 1090), for a yield of the major peak of ca. 85% purity (at UV 254). The peak at 9.73 appears to be benzoyl chloride, and that at 11.68 appears to be benzoic acid, based on authentic standards.

EXAMPLE 3

Evaluation of Synergistic Activity

The pinto bean-based diet was then added in 5-ml quantities to test tubes. The test tubes were held at 60° C. until the chemicals were incorporated to prevent solidification of the diet. The insecticide and kojic acid were added in 125 μl acetone to the liquid diet to give a final concentration as indicated in Table I. The chemicals were incorporated into the diets by blending vigorously with a vortex mixer for 20 sec. Preliminary observations with colored solutions of both water and acetone indicated uniform incorporation by this method. The diets were dispensed into culture plates, and allowed to cool to room temperature. To remove the potentially toxic acetone, the diets were placed in a fume hood for ca. 20 min until slight darkening occurred. All diets were treated in the same way. The diets were cut into approximately equal sections, and each section was placed into a well of a 24-well immunoassay plate. A single neonate *H. zea* or *S. frugiperda* larvae was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4, and 7 days, and the surviving larvae were weighed after 7 days. Each chemical set was tested on a total of 40 larvae.

Results of the evaluations are shown in Table I below.

It is understood that the foregoing detailed description is given merely by way of illustration and that modification and variations may be made therein without departing from the spirit and scope of the invention.

TABLE I

| | % Mortality | |
|---|---|---|
| Compound | Fall armyworm *S. frugiperda* | Corn earworm *H. zea* |
| None (Control) | 0 | 0 |
| Kojic acid (250 ppm) | 0 | 0 |
| Pyrethrins (0.25 ppm) | 57.5 | 28.9 |
| Pyrethrins (0.25 ppm) Kojic acid (250 ppm) | 97.4 | 57.5 |
| Pyrethrins (0.25 ppm) Dibenzoyl kojic acid (25 ppm) | — | 57.1 |

TABLE I-continued

| Compound | % Mortality Fall armyworm S. frugiperda | % Mortality Corn earworm H. zea |
|---|---|---|
| Allethrin (0.25 ppm) | — | 7.5 |
| Allethrin (0.25 ppm) Kojic acid (250 ppm) | — | 27.5 |
| Carbaryl (0.25 ppm) | 0 | 36.8 |
| Carbaryl (0.25 ppm) Kojic acid (250 ppm) | 8.1 | 47.5 |
| Carbofuran (0.25 ppm) | 47.5 | 69.2 |
| Carbofuran (0.25 ppm) Kojic acid (250 ppm) | 61.0 | 80.6 |

I claim:

1. A composition for controlling Lepitopteran insects comprising: (1) an insecticidally effective amount of insecticide selected from the group consisting of pyrethrins, pyrethroids, and carbamates; (2) a synergistically effective amount of kojic acid or an ester of kojic acid, wherein the kojic acid or kojic acid ester is present in the range of about 25 to 250 ppm; and (3) an agronomically acceptable carrier.

2. A composition as described in claim 1 wherein said insecticide is one or more pyrethrins.

3. A composition as described in claim 1 wherein said insecticide is one or more pyrethroids.

4. A composition as described in claim 1 wherein said insecticide is the pyrethroid, allethrin.

5. A composition as described in claim 1 wherein said insecticide is the carbamate, carbaryl.

6. A composition as described in claim 1 wherein said insecticide is the carbamate, carbofuran.

7. A composition as described in claim 1 wherein said ester of kojic acid is dibenzoyl kojic acid.

8. A composition as described in claim 1 wherein the insecticide: kojic acid ester ratio is in the range of 1:100 to 1:1000.

9. A method for controlling Lepitopteran insects comprising applying to the habitat of said insects an insecticidally effective amount of a composition comprising: (1) an insecticide selected from the group consisting of pyrethrins, pyrethroids, and carbamates; (2) a synergistically effective amount of kojic acid or an ester of kojic acid, wherein the kojic acid or kojic acid ester is present in the range of about 25 to 250 ppm; and (3) an agronomically acceptable carrier.

10. A method as described in claim 9 wherein said insecticide is one or more pyrethrins.

11. A method as described in claim 9 wherein said insecticide is one or more pyrethroids.

12. A method as described in claim 9 wherein said insecticide is the pyrethroid, allethrin.

13. A method as described in claim 9 wherein said insecticide is the carbamate, carbaryl.

14. A method as described in claim 9 wherein said insecticide is the carbamate, carbofuran.

15. A method as described in claim 9 wherein said ester or kojic acid is dibenzoyl kojic acid.

* * * * *